United States Patent [19]
Chikawa

[11] 3,944,823
[45] Mar. 16, 1976

[54] X-RAY TOPOGRAPH REPRODUCING APPARATUS

[75] Inventor: Junichi Chikawa, Tokyo, Japan
[73] Assignee: Nippon Hoso Kyokai, Tokyo, Japan
[22] Filed: July 15, 1974
[21] Appl. No.: 488,682

Related U.S. Application Data

[63] Continuation of Ser. No. 325,414, Jan. 22, 1973, abandoned, which is a continuation of Ser. No. 123,726, March 12, 1971, abandoned.

[30] Foreign Application Priority Data

| Mar. 16, 1970 | Japan | 45-21613 |
| Apr. 23, 1970 | Japan | 45-34516 |
| Apr. 23, 1970 | Japan | 45-34517 |

[52] U.S. Cl. ............ 250/274; 250/277 CH
[51] Int. Cl.² ........................ G01M 23/20
[58] Field of Search ......... 250/272, 273, 274, 275, 250/276, 277, 278, 279

[56] References Cited
UNITED STATES PATENTS

| 2,897,371 | 7/1959 | Hasler | 250/276 |
| 3,015,027 | 12/1961 | Burst | 250/272 |
| 3,336,494 | 8/1967 | Nagashima | 250/272 |
| 3,582,651 | 6/1971 | Siedband | 250/274 |
| 3,609,356 | 9/1971 | Schwuttke | 250/277 |

Primary Examiner—Craig E. Church
Attorney, Agent, or Firm—Stevens, Davis, Miller & Mosher

[57] ABSTRACT

An X-ray topograph reproducing apparatus is provided whereby the X-ray topograph throughout the total surface of a specimen crystal may be reproduced in positive and rapid succession. The reproduction of the X-ray topograph is effected by providing means for rotating the crystal in a horizontal direction while being moved in parallel with a given direction. The X-ray topograph at one point on the crystal obtained by an incident X-ray having different wave lengths is always reproduced at the same position on a record surface by providing means for maintaining the amount of movement of the record surface with respect to the amount of movement of the crystal at a given ratio and by providing means for recording or indicating an image reproducing output signal in one or two dimensional manner by both of a signal of detecting the amount of movement of the crystal and a signal associated with scanning in the lengthwise direction of slits through which pass the X-ray.

5 Claims, 13 Drawing Figures

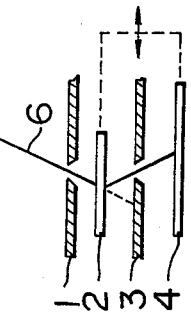
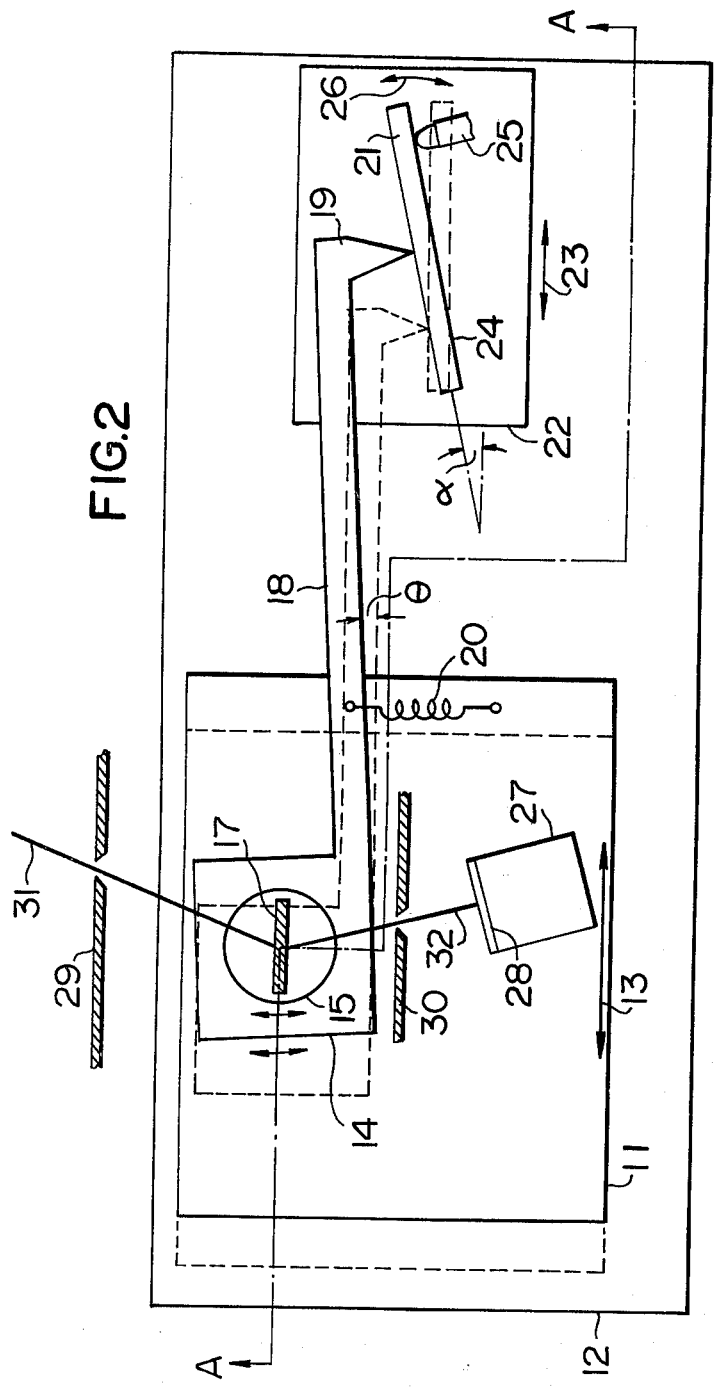
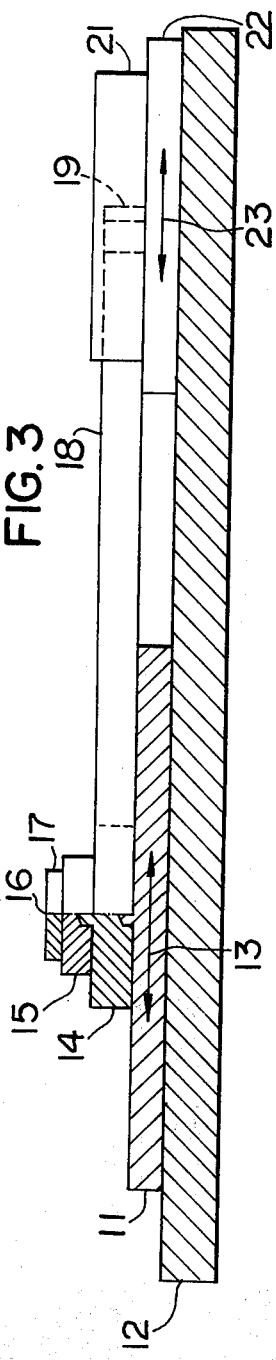

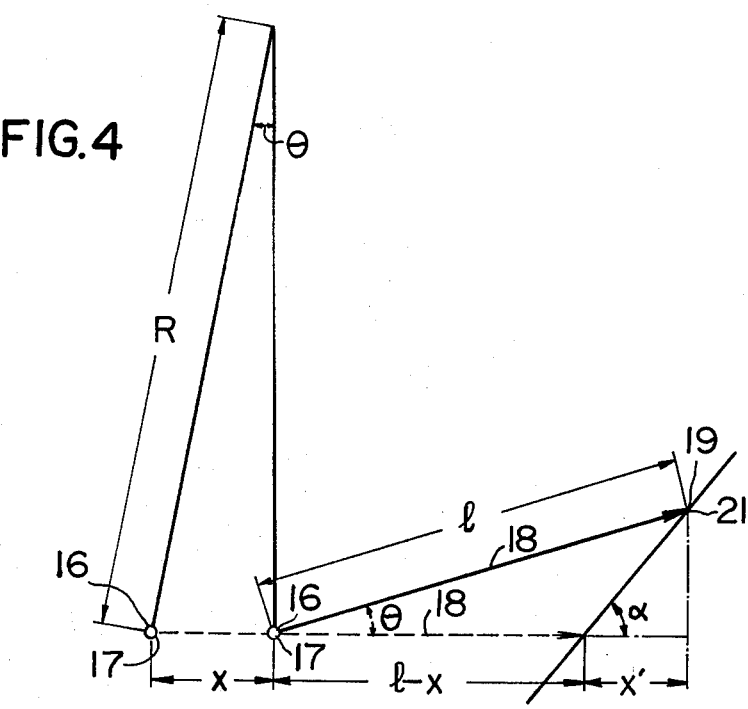
FIG.4
FIG.6    FIG.5
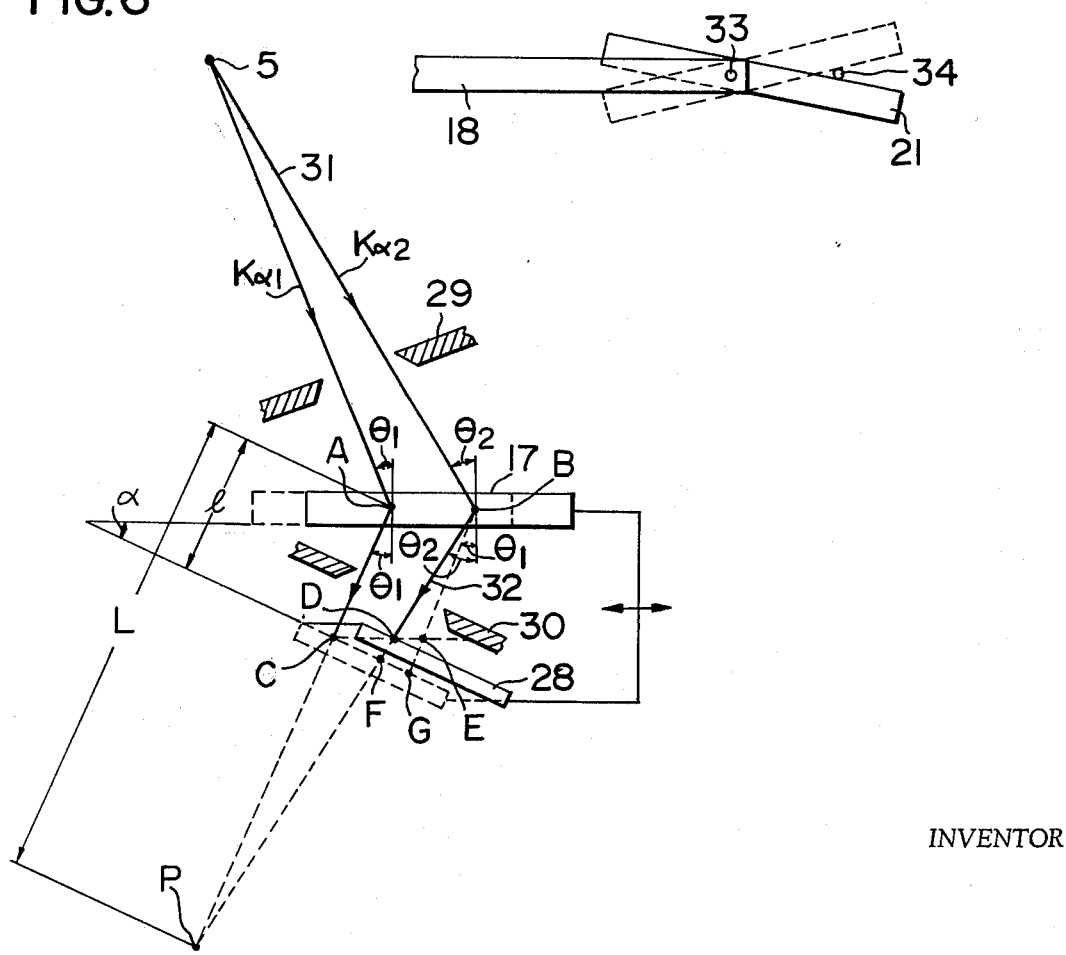

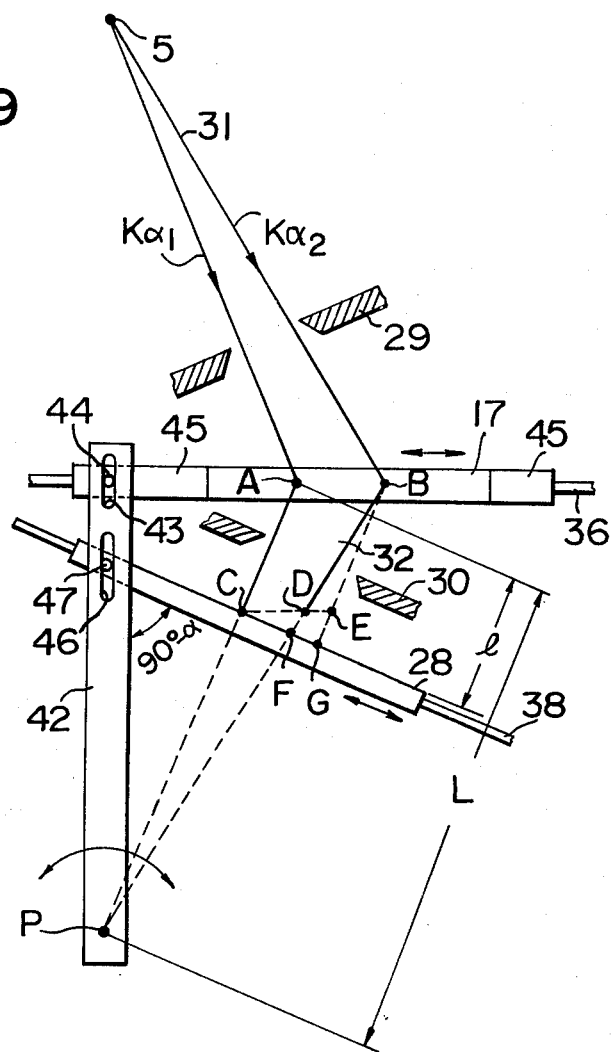
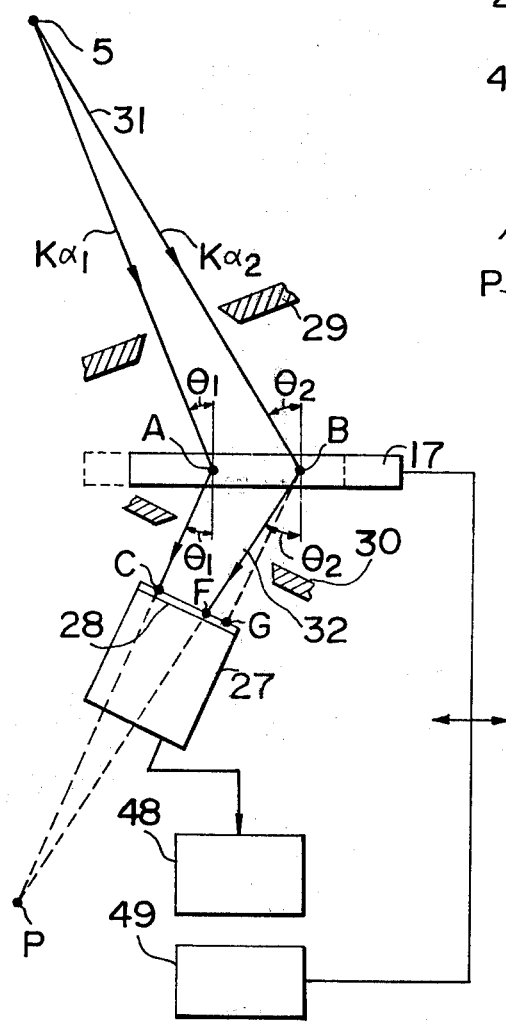

X-RAY TOPOGRAPH REPRODUCING APPARATUS

This is a continuation of application Ser. No. 325,414, filed Jan. 22, 1973, which is a continuation of application Ser. No. 123,726, filed Mar. 12, 1971 both abandoned.

BACKGROUND OF THE INVENTION FIELD OF THE INVENTION

The present invention relates to an X-ray topograph reproducing apparatus, more particularly, to an improved apparatus which can correct an incident angle of an X-ray beam arriving at the surface of a specimen crystal such that Bragg's diffraction condition is satisfied, that is, the incident angle is always equal to Bragg's angle and hence the X-ray topograph (X-ray microscopically diffracted image) throughout the total surface of the crystal can be reproduced and recorded irrespective of the presence of absence of curved portions formed thereon.

DESCRIPTION OF THE PRIOR ART

A Lang's camera, that is, an X-ray topograph camera of the scanning type heretofore proposed and shown in FIG. 1 comprises two stationary slits 1 and 3, a specimen crystal 2 whose crystal defect is to be measured and a photographic dry plate 4, and in which the crystal 2 and the photographic dry plate 4 are operatively interlocked to reciprocate in parallel with one another in a given direction shown by arrows such that the Bragg's diffraction condition is satisfied. An X-ray beam 6 emitted from an X-ray supply source 5 whose focal point is extremely small and incident through the first slit 1 upon the crystal 2 causes Bragg's reflection. A straight path undergone by the X-ray 6 shown by dotted lines is interrupted by the second slit 3 and the diffracted beam only is incident through the second slit 3 upon the photographic dry plate 4 to reproduce a diffracted image of the crystal 2 thereon.

In the above mentioned X-ray topograh camera of the scanning type, the incident angle of the X-ray beam 6 must always satisfy Bragg's diffraction condition. In cases of reproducing an X-ray topograph of the surface of a crystal having minutely curved portions, Bragg's diffraction condition is only satisfied by one curved portion of the crystal so that at every time of reproducing the X-ray topograph only a diffracted image of one of the curved portions of the crystal can be reproduced. Thus, it is very troublesome to reproduce the X-ray topograph throughout the total surface of the crystal with the aid, for example, of a television camera.

When the crystal structure is to be examined in a laboratory, specimen crystals whose diffracted images can easily be reproduced are selected in order to avoid the trouble of reproducing the X-ray topograph thereof. But, in case of manufacturing semiconductor wafers the surface of a crystal such as silicon becomes minutely curved owing to the heat treatment given to the crystal during the manufacturing steps, with the result that it is often necessary to detect the crystal defects included in such minutely curved portions with the aid of the X-ray topograph. Thus, that position of the crystal at which the diffracted image should be reproduced must frequently be changed in order to detect the crystal defect throughout the total surface of the crystal. Such adjustable and frequent changes of the position of the crystal make the steps of manufacturing the semiconductor wafer very difficult and quite unsuitable for carrying out such steps in an industrial scale.

The X-ray beam 6 emitted from the X-ray supply source 5 is a characteristic X-ray $K\alpha$ beam consisting of two spectral lines $K\alpha_1$ and $K\alpha_2$ whose diffraction directions are slightly different from each other. The irradiation of the crystal with two spectral lines $K\alpha_1$ and $K\alpha_2$ results in a record of two diffracted images of the crystal which are slightly shifted from each other thus deteriorating the resolving power of the record thus obtained. In order to improve the resolving power of the record, it has heretofore been proposed to interrupt the $K\alpha_2$ of the two spectral lines by means of a mechanical slit. Such interruption of the spectral line $K\alpha_2$ decreases the diffraction strength of the X-ray beam. Use has also been made of a narrow slit to separate $K\alpha_1$ of the two spectral lines from spectral line $K\alpha_2$. In this case the reflecting surface of the crystal must strictly be in parallel with the lengthwise direction of the slit, thus requiring a large expenditures of time and effort for adjusting the position of the crystal. Moreover, the use of spectral line $K\alpha_1$ only could not improve the resolving power of the record obtained even though the focal point of the X-ray beam is made as small as possible since spectral line $K\alpha_1$ per se has also different wave lengths over a considerable range. Thus, the conventional X-ray topograph reproducing apparatus could not be applied for the steps of manufacturing a semiconductor wafer in an industrial scale.

SUMMARY OF THE INVENTION

It is accordingly an object of the invention to provide an improved X-ray topograph reproducing apparatus which can improve the resolving power of diffracted images.

Another object of the invention is the provision of an improved X-ray topograph reproducing apparatus suitable for use in detecting crystal defects of a semiconductor wafer.

A still further object of the invention is the provision of an improved X-ray topograph reproducing apparatus whih can detect the crystal defect of a crystal having minutely curved surface portions in a rapid and easy manner.

It is a particular object of the invention to provide an improved X-ray topograph reproducing apparatus which can be remotely controlled to prevent an operator from being exposed to dangerous X-ray beams.

According to the invention there is provided an improved X-ray topograph reproducing apparatus comprising means of supporting a specimen crystal to be measured having flat or curve surface portions so as to rotate the specimen crystal in a horizontal direction while being moved in parallel with a given direction, an arm projecting from said supporting means and having a desired length and provided at its free end with a guide member, a straight guide rail associated with said guide member to rotate said crystal in a horizontal direction in response to its movement in parallel with said given direction, and means for adjusting the inclined angle of said guide rail with respect to said given direction, and which is arranged in a manner such that an incident angle of an X-ray beam arriving at the surface of said crystal is made equal to the Bragg's angle at every position of said crystal so that the diffracted image of the crystal throughout the total surface thereof can be reproduced in a positive and easy manner.

According to the invention there is further provided an improved X-ray topograph reproducing apparatus comprising means for maintaining the amount of movement of a record surface such as a picture screen of a television camera or a photographic dry plate of a photographic camera with respect to the amount of movement of a specimen crystal at a given ratio determined by the geometrical arrangement between an X-ray supply source on the one hand and the crystal and the record surface on the other hand, and which is arranged in a manner such that the X-ray topograph at one point on the crystal obtained by an incident X-ray having different wave lengths is always reproduced at the same position on the record surface.

According to the invention there is still further provided an improved X-ray topograph reproducing apparatus comprising means including a stationary record surface and for scanning it to deliver an image reproducing output signal, means for extracting an image reproducing output signal corresponding to an X-ray topograph having a desired range of wave lengths from X-ray topographs formed on a record surface such as a picture screen of a television camera or a photographic dry plate of a photographic camera, and means receiving said image reproducing output signal as extracted by said extracting means and a signal associated with scanning in the lengthwise direction of slits on the one hand and a signal derived in correspondence with the movement of a specimen crystal and for detecting the amount of movement of said crystal and recording or indicating said image reproducing output signal in one or two dimensional manner by both of said signal of detecting the amount of movement of the crystal and of said signal associated with said scanning in the lengthwise direction of the slits.

Preferred embodiments of the invention are illustrated in the following drawings in which:

BRIEF DESCRIPTION OF THE DRAWINGS

FIG. 1 is a schematic illustration of a conventional X-ray topographic reproducing apparatus;

FIG. 2 shows a plan view of an X-ray topograph reproducing apparatus comprising means of mechanically correcting an incident angle of an X-ray beam arriving at the surface of a crystal specimen so as to always satisfy the Bragg's diffraction condition;

FIG. 3 is a sectional view taken along the line A—A of FIG. 2;

FIG. 4 is a schematic representation illustrating the operation of the apparatus shown in FIG. 2;

FIG. 5 is a plan view of a variant of a detail of FIG. 2; and

FIG. 6 shows diagrammatically a fundamental construction of the X-ray topograph reproducing apparatus according to the invention for illustrating its principle and adapted to prevent a deterioration of the resolving power caused by the aberration produced by the difference in diffraction directions of two spectral lines $K\alpha_1$ and $K\alpha_2$ of the characteristic X-ray;

FIGS. 7 to 10 show diagrammatically various embodiments of the X-ray topograph reproducing apparatus constructed on the basis of the principle illustrated in FIG. 6;

DESCRIPTION OF THE PREFERRED EMBODIMENTS

Figure 11:
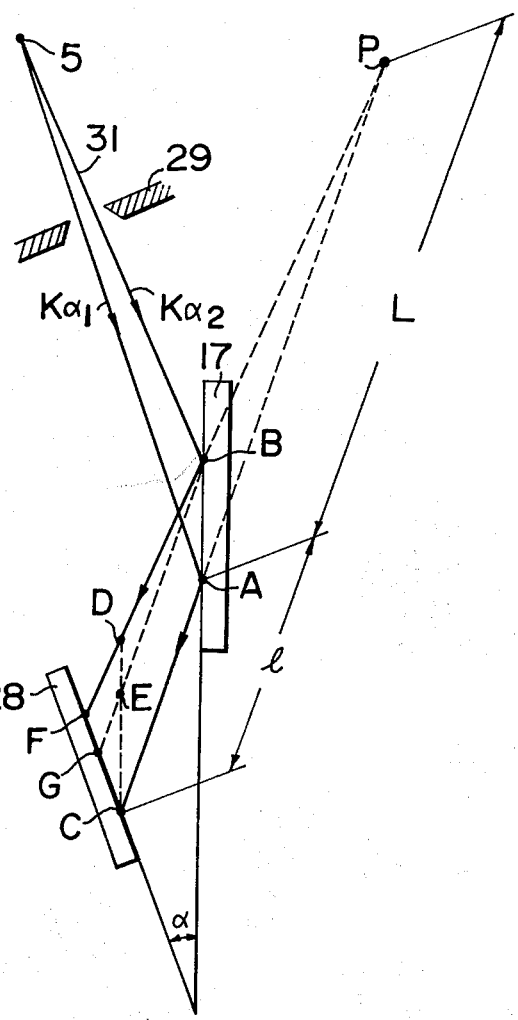
FIG. 11 shows diagrammatically another embodiment of the X-ray topograph reproducing apparatus applied to the Bragg case wherein diffracted images are obtained by X-ray reflection.

Referring to FIGS. 2 and 3, 11 designates a carriage movably on a bed 12 so as to be movable along the surface of the bed 12 in a direction shown by arrows 13. 14 shows a block which is rotatable about its center axis 16 on the surface of the carriage in a direction shown by arrows and on which is rotatably mounted a table 15 which is also rotatable about the center axis 16. The table 15 is made stationary after it has been rotatably adjusted on the block 14. The block 14 is provided on its one side with arm 18 projected therefrom and having a desired length and extending in a direction in parallel with a specimen crystal 17 whose crystal defects are to be measured. The arm 18 is provided at its free end with a claw-shaped guide member 19 which is urgent against a straight guide rail 21 by means of a tension spring 20 arranged between the arm 18 and the carriage 11. 22 designates another carriage adapted to move in a direction shown by arrows 23. On this carriage 22 is arranged the guide rail 21. When the arm 18 occupies a position shown by dotted lines which is coincident with the horizontal direction, the guide claw 19 comes into contact with the guide rail 21 at a point 24 which will hereinafter be called as a first adjusted point. The guide rail 21 is adapted to rotate about this point 24 in a direction shown by arrows 26 with the aid of an adjustable member 25 for adjusting the inclined angle $\alpha$ of the guide rail 21. The guide rail 21 is made stationary after it has been rotatably adjusted to a desired inclined position. 27 shows a diffracted image reproducing means such as a television camera or a photographic camera secured to the carriage 11 and adapted to reproduce an X-ray topograph. The diffracted image reproducing means 27 is so arranged that its record surface 28 such as a picture screen or a photographic dry plate may be moved in parallel with the direction 13 whilst making the angle of the record surface 28 inclined from the surface to be measured of the crystal 17 constant. 29 shows a first slit arranged between an X-ray supply source (not shown) and the crystal 17. 30 is a second slit arranged between the crystal 17 and the record surface 28. All of the X-ray supply source and the first and second slits 29 and 30 are secured to the bed 12.

If the carriage 11 moves in the direction shown by the arrows 13, the crystal 17 and the record surface 28 move in parallel with the direction 13 so that the total surface to be measured of the crystal 17 is scanned by an incident X-ray beam 31 to reproduce a diffracted image of the crystal 17 on the record surface 28.

In case of continuously reproducing the diffracted image of the crystal 17, at the first place where the crystal 17 has minutely curved surface portions such as refound in a silicon monocrystal the carriage 11 is moved to a position shown by dotted lines where the guide claw 19 is located at the first adjusted point 24 on the guide rail 21 and the arm 18 extends in a horizontal director as shown in dotted lines. Then, the table 15 is so rotated that the incident angle of the X-ray beam 31 is equal to the Bragg's angle and that the X-ray beam 32 is incident through the second slit 30 upon the record surface 28 and then the table 15 is secured to the block 14. Secondly, that position at which the crystal 17 is moved towards a position shown by full line the adjustable member 25 is moved in a direction shown by arrows 26 to adjust the inclined angle a of the guide rail 21.

The curvature of the curved surface of the crystal 17 is extremely small and is substantially similar to a circle. If the inclined angle $\alpha$ of the guide rail 21 is so adjusted that the incident angle of the X-ray beam 31 is equal to the Bragg's angle at the above mentioned two positions, the adjustments at these two positions cause the surface of the crystal 17 to trace a given circle. Thus, the incident angle of the X-ray beam 31 inclined from a tangent line at the position of arrival at the crystal 17 of the incident X-ray beam 31 becomes constant. As seen from the above, the incident angle of the X-ray beam 31 is equal to the Bragg's angle so that the Bragg's diffraction condition is satisfied by the crystal 17 throughout its movement, thereby continuously reproducing the diffracted image of the crystal 17 on the record surface 28.

The geometrical relation between the crystal 17 on the one hand and the arm 18 and the guide rail 21 on the other hand will now be described. A simplified construction of the apparatus shown in FIG. 2 is diagrammatically illustrated in FIG. 4. The positions of the arm 18 and the crystal 17 shown by dotted lines and full line in FIG. 4 (these positions corresponds to those positions at their rotating center axis 16 shown in FIG. 3) correspond to the positions of the arm 18 and the crystal 17 shown by dotted lines and full line in FIG. 2.

If the length of the arm 18 is $l$, the distance moved by the rotating center axis 16 $x$, the length of displacement in the horizontal direction of the guide claw 19 $x'$ and the angular change of the arm 18 with respect to the horizontal direction $\theta$, then $$x' = x - l(1 - \cos \theta) \quad (1)$$

$$x' \tan \alpha = l \sin \theta \quad (2)$$

where $\theta$ is extremely and hence $1 - \cos \theta \simeq 0$ and $\sin \theta \simeq \theta$.
Then
$$x' \simeq x$$
and from the equation (2)

$$x = \frac{l}{\tan \alpha} \theta \quad (3)$$

The equation (3) represents a circle having a radius of curvature R given by $$R = \frac{l}{\tan \alpha} \quad (4)$$

Thus, the above mentioned two points of adjustment makes it possible to always keep the incident angle $\theta$ of the X-ray beam 31 inclind from the tangential direction of the locus traced by the crystal 17 constant.

In the embodiment shown in FIG. 2, if the crystal 17 is positioned on the rotating center axis 16 of the table 15 and $l = 20$ cm, $x = 3$ cm, $\theta = 2'$ and $$\tan \alpha = \frac{120 \mu m}{30 \ mm}$$

($\alpha = 0.23°$), then the radius of curvature R is given by the equation (4) as 50 m.

The inclined angle $\alpha$ of the guide rail 21 determined by the adjustable member 25 is equal to the curvature of the above mentioned curved surface of the crystal 17. Thus, the measurement of such inclined angle $\alpha$ ensures an indications of the curvature of the curved surface of the specimen 17.

In the above mentioned embodiment, it is not always necessary to attend the arm 18 along the direction of movement of the crystal 17, but it is preferred. Because, if the length l of the arm 18 is constant, the adjustment of the angular change of the position of the crystal 17, that is, the rate of magnification of the inclined angle $\alpha$ of the guide rail 21 reaches a maximum.

If the inclined angle $\alpha$ of the guide rail 21 changes from zero to positive as shown in FIG. 2 or from zero to negative or from any angle to zero with respect to the direction of movement of the crystal 17, the locus traced by the crystal 17 becomes a concave, convex or flat surface respectively.

If the angle $\theta$ of the arm 18 with respect to the horizontal direction is extremely small and the arm 18 extends along the horizontal direction, the first adjusted point 24 can be adjusted by moving it along the horizontal direction, and then the above mentioned adjustments of the table 15 and the guide rail 21 can be carried out.

The arm may be provided at its free end with a pivot pin 33 about which may pivot the guide rail 21 as shown in FIG. 5. In the present embodiment, the pivot pin 33 serves to adjust the inclined angle $\alpha$ of the guide rail 21. After the guide rail 21 has been secured to its adjusted inclined position, the guide rail 21 is brought into engagement with a guide pin 33 secured to the carriage 22. The present embodiment is also capable of making the incident angle of the x-ray beam 31 equal to the Bragg's angle.

Thus, the invention provides an efficient way of continuously reproducing the X-ray topograph of the crystal 17 througout the total surface thereof even when the crystal surface is minutely curved in a manner similar to the case when the crystal surface is flat irrespective of the presence of the concave or convex surface and can be applied effectively to the X-ray diffraction analysis of the semiconductor wafer whose crystal surface includes curved portions produced when subjected to the heat treatment during the manufacture thereof and further provides the important industrial advantage that the X-ray diffraction analysis can be performed on line.

The apparatus according to the invention may suitably be applied to apparatus in which the incident angle of a radiation beam must be corrected as in the case of measuring the transmittivity of the specimen crystal with the aid of the electron beam or light ray other than the X-ray beam.

In FIG. 6 there is shown another embodiment of the X-ray topograph reproducing apparatus according to the invention in which use is made of the X-ray beam of characteristic X-ray $K\alpha$ beam consisting of two spectral lines $K\alpha_1$ and $K\alpha_2$ whose diffraction directions are slightly different one from the other. In the present embodiment, the first slit 29 arranged between an X-ray supply source 5 having an extremely small focal point and the crystal 17 and the second slit 30 arranged between the crystal 17 and the record surface 28 are made stationary, whereas the crystal 17 and the record surface 28 are made reciprocated at the same speed and parallel to one another in a direction shown by arrows in a manner such that the incident angle of the X-ray beam 31 is equal to the Bragg's angle.

The characteristic X-ray K$\alpha$ beam 31 issued from the X-ray supply source 5 and consisting of the two spectral lines K$\alpha_1$ and K$\alpha_2$ is incident through the first slit 29 upon the crystal 17 to cause Bragg's diffraction thereon. A straight path (not shown) undergone by the X-ray 31 is interrupted by the second slit 30 and the diffracted X-ray 32 only is incident through the second slit 30 upon the record surface 28 to reproduce the diffracted image of the crystal 17 thereon.

Let the wave lengths of the characteristic X-ray spectral lines K$\alpha_1$ and K$\alpha_2$ be designated as $\lambda_1$ and $\lambda_2$ ($\lambda_1 < \lambda_2$), respectively, and let the distance between atoms of the crystal 17 be designated as d. The Bragg's angles $\theta_1$ and $\theta_2$ for $\lambda_1$ and $\lambda_2$ are $\theta_1 < \theta_2$ since $2d\sin\theta_1 = \lambda_1$ and $2d\sin\theta_1 = \lambda_2$. Thus, the Bragg's angle $\theta_1$ at a point A on the crystal 17 is different from the Bragg's angle $\theta_2$ at another point B thereon, with the result that the position of the diffracted X-ray 32 of the K$\alpha_1$ spectral line is shifted from the position of the diffracted X-ray small of the K$\alpha_1$ spectral line. If the focal point of the X-ray supply source 5 is extremely small and the distance between the X-ray supply souce 5 and the crystal 17 is considerably large, those points on the crystal 17 at which the K$\alpha_1$ and K$\alpha_2$ spectral lines satisfy the Bragg's condition are separated into the points A and B on the crystal.

More particularly, if the crystal 17 having the lattice defect at the point A moves across the K$\alpha_1$ spectral line in the direction shown by arrows, the lattice defect point A causes the K$\alpha_1$ spectral line to diffract and reproduce its diffracted image at a point C on the record surface 28. When the lattice defect at the point A reaches the position B of the K$\alpha_1$ spectral line, the movement of the record surface 28 moved with the crystal 17 at the same speed results in a displacement of the point C at which has been reproduced the diffracted image towards a point E, while the diffracted image of the same lattice defect is reproduced at a point D, with the result that the diffracted images of the spectral line K$\alpha_1$ and K$\alpha_2$ are reproduced at different positions thus deteriorating the resolving power of the record obtained.

The invention, by taking the above mentioned fact into consideration, causes the movement of the record surface 28 to lag with respect to the movement of the crystal 17 by a distance $\overline{DE}$ and bring the diffracted image C into coincidence with the diffracted image D and hence improve the resolving power of the diffracted image.

Let a point of symmetry of the X-ray supply source 5 with respect to the position of the crystal 17 taken as a symmetrical plane, that is, a point into which are converged the diffracted images of the K$\alpha_1$ and K$\alpha_2$ spectral lines be designated as a point F and let points at which intersect extensions of straight lines BD and BE which extend through the two points D and E, respectively, with the record surface 28 shown by dotted lines be designated as F and G, respectively. Moreover, let the distance between the crystal 17 and the record surface 28 shown by dotted lines be designated as E = $\overline{AC}$ and let the distance between the point F and the crystal 17 be designated as L = $\overline{AP}$. Then, the ratio between the amount of movement $\overline{AB}$ of the crystal 17 and the amount of movement $\overline{CP}$ of the record surface 28, that is the ratio between the amounts of movement $$\frac{\overline{CP}}{\overline{AB}}$$

is given by $$\frac{\overline{CP}}{\overline{AB}} \cdot \frac{\overline{CD}}{\overline{AB}} = \frac{\overline{CP}}{\overline{AP}} = \frac{L-l}{L}.$$

Thus, the crystal 17 and the record surface 28 may be operatively interlocked such that the two diffracted images of the spectral lines K$\alpha_1$ and K$\alpha_2$ are disposed one upon the other to record a diffracted image having a good definition.

The above mentioned distance $\overline{CD}$ is a distance measured in parallel with the crystal 17 and is not equal to the amount of movement $\overline{CF}$ of the record surface 28. But, the angle a between the crystal 17 and the record surface 28 is about 6° to 10°, the amount of movement of the crystal 17 is about 2 cm and the distance between the x-ray supply source 5 and the crystal 17 is about 50 cm.

Thus an assumption may be made that $\overline{CD} = \overline{CF}$ and the distances l and L are constant during the movement of the crystal 17.

Figure 7:
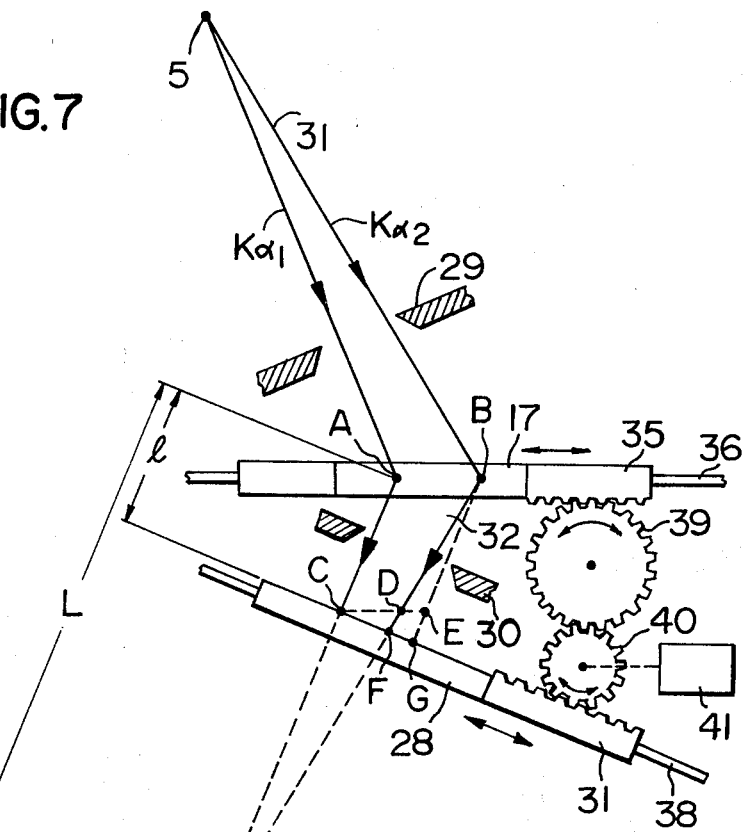

Referring now to FIG. 7 showing a further embodiment of the apparatus according to the invention, 35 designates a rack for supporting and moving the crystal 17 along a guide member 36 such as a rail. 37 shows another rack for supporting and moving the record surface 28 along a guide member 38 such as a rail. The rack 35 is threadedly engaged with a gear 39 which is in mesh with a gear 40 with which is threadedly engaged the rack 37. One of the gears 40 is driven by a driving means 41 such as a motor, etc. The gear ratio between the gears 39 and 40 is determined by $$\frac{\text{Number of teeth of gear 39}}{\text{Number of teeth of gear 40}} = \frac{L}{L-l}.$$

Thus, the ratio between the amounts of movement of the racks 35 and 37 is given by $$\frac{\text{Amount of movement of the rack 35}}{\text{Amount of movement of the rack 37}} = \frac{L}{L-l}$$

This ratio ensures a record of the two diffracted images of the same lattice defect of the crystal 17 at the same position on the record surface 28.

As seen from the above, the invention permits the diffracted image of the same lattice defect upon which is incident the x-ray beam 31 having two spectral lines K$\alpha_1$ and K$\alpha_2$ to be reproduced always at the same position on the record surface 28. The invention may also be applied to a continuous x-ray without any modification.

A modified embodiment of moving the crystal 17 and the record surface 28 whilst maintaining the above mentioned ratio between the amounts of movement constant will now be described with reference to FIG. 8.

Figure 8:
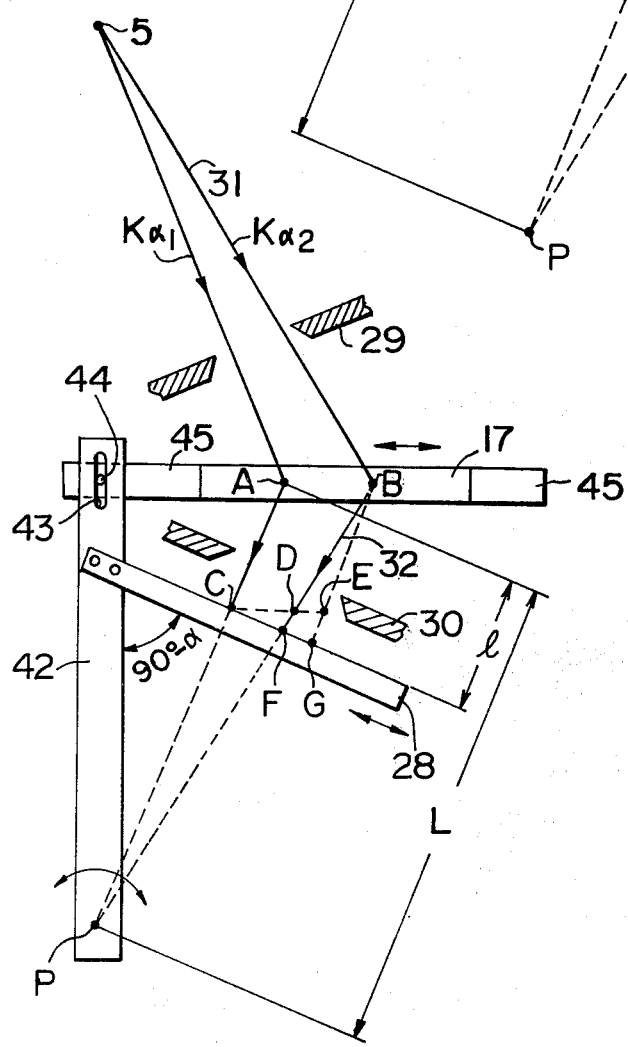

Referring to FIG. 8, let a point of symmetry of the x-ray supply source 5 with respect to the crystal 17 taken as a symmetrical plane be designated as a point P. Then, the diffracted images of the two spectral lines $K\alpha_1$ and $K\alpha_2$ are converged into the point P. In the present embodiment about the point P is pivotally mounted an arm 42 to which is secured the record surface 28 inclined by an angle of $90° - a$ from the arm 42. The arm 42 is provided at its free end with a guide groove 43 into which is slidably engaged a pin 44 secured to a member 45 for supporting the crystal 17.

If the arm 42 is rotated, the crystal 17 and the record surface 28 move in a direction shown by arrows with the ratio between the amounts of movement kept constant to reproduce the x-ray topograph of the same lattice defect at the same position on the record surface 28.

Thus, the invention is capable of using the first slit 29 whose width is sufficiently wide enough to pass the x-ray beam 31.

In FIG. 9 there is shown a variant of the embodiment shown in FIG. 8. In the present embodiment, the crystal supporting member 45 and the record surface 28 are so arranged that they can be moved along guide members 36 and 38 such as rails inclined one from the other by the angle $\alpha$. The arm 2 is rotatably mounted about the above mentioned point P and is provided at its free end with two guide grooves 43 and 46 into which are slidably engaged pins 44 and 47 secured to the crystal supporting member 45 and the record surface 28, respectively. Similar to the embodiment shown in FIG. 8, if the arm 42 is rotated, the crystal 17 and the record surface 28 move along the guide members 36 and 38 in directions shown by arrows with the above mentioned ratio between the amounts of movement kept constant.

FIG. 10 shows a still further embodiment of the apparatus according to the invention wherein use is made of an x-ray Vidicon tube as the diffracted image reproducing means 27.

In the embodiment shown in FIG. 10, the diffracted x-ray 32 is incident upon the picture screen 28 of the x-ray Vidicon tube 27 to reproduce the diffracted image of the crystal 17 thereon. An electric signal corresponding to the diffracted image is delivered to a monitor 48 which serves to treat the electric signal such that the diffracted image on the picture screen 28 is magnified in a direction in parallel with the slits 29 and 30 and perpendicular to the sheet of FIG. 5 by M times larger than the original diffracted image and is magnified in a direction CF by M times larger than an inverse number of the above mentioned constant ratio between the amounts of movement, i.e., $L/L$-A, thus enabling the diffracted image to be recorded by a recording means 49. In the present embodiment, the x-ray Vidicon tube 27 and the monitor 48 are made stationary, whilst the crystal 17 and the recording means 49 are moved in synchronism and also in parallel with one another in a direction shown by arrows. The scanning of the recording means 49 is effected at a speed which is M times faster than that of the scanning of the crystal 17.

In the present embodiment, the use of the monitor 48 and the recording means 49 makes it possible to shift, when the crystal 17 is moved, the diffracted image C of the lattice defect point A of the crystal 17 obtained by the $K\alpha_1$ spectral line not to a point O on the record surface 28 but to diffracted image P of the lattice defect point A of the crystal 17 obtained by the $K\alpha_2$ spectral line. Thus, the diffracted images recorded by the monitor 48 and the recording means 49 and corresponding to the diffracted images C and P, respectively, are disposed one upon the other to improve the resolving power of the diffracted image.

All of the embodiments shown in FIGS. 7 to 10 are applied to the Laue case in which diffracted images are obtained by X-ray transmission. The invention may also be applied to the Bragg case wherein diffracted images are obtained by X-ray reflection as shown in FIG. 11.

In the embodiment shown in FIG. 11, the above mentioned ratio between the amounts of movement is replaced by a ratio given by $$\frac{\overline{CP}}{\overline{AB}} \cdot \frac{\overline{CD}}{\overline{AB}} = \frac{L+l}{L}.$$

In the present embodiment the moving means is constructed such that the crystal 17 is operatively interlocked with the record surface 28 with the ratio $L+l/L$ kept as in the embodiments shown in FIGS. 7 to 10.

In case of obtaining the diffracted image by X-ray reflection as in the Bragg case with the aid of the television camera similar to the embodiment shown in FIG. 10 use may be made of the ratio $L/L+l$ in place of the ratio $L/L-1$.

As seen from the above, the invention makes it possible to use the slit 29 whose width is sufficiently wide enough to pass all of the X-ray beams 31 and eliminate a difficult problem of accurately adjusting the crystal position which has been encountered with the conventional apparatus thereby adjusting the crystal position without any skill in a rapid and simple manner. The present invention also permits the same lattice defect of the specimen crystal to be disposed one upon the other and recorded at the same position on the record surface 28 or by the recording means 49. Thus, the strength of the diffracted images of the $K\alpha_1$ and $K\alpha_2$ spectral lines can be increased about 1.5 times stronger than the diffracted images obtained by the conventional apparatus. Thus, the invention is particularly useful in case of reproducing the X-ray topograph of the diffracted image.

The Lang's camera heretofore proposed has its resolving power in the order of at most 2 to 3 $\mu$m even in the presence of the extremely small focal point owing to the enlargement in the range of the wave lengths of the $K\alpha_1$ spectral line. The invention ensures convergence of the refracted images of all of the different wave lengths of the X-ray beams into one point and hence can eliminate an adverse effect due to the enlargement in the range of the different wave lengths of the X-ray beam with the result that the use of an X-ray tube whose X-ray focal point is small permits of obtaining a high resolving power in the order of 0.1 $\mu$m in an easy manner.

In the above mentioned embodiments, the characteristic X-ray $K\alpha_1$ and $K\alpha_2$ lines consist of spectral lines having different wave lengths. But, the similar advantageous effect can also be obtained by using a continuous X-ray in place of the characteristic X-ray without deteriorating the resolving power of the diffracted image. For example, an X-ray having a wave length which lies near the absorption end may be used to reproduce an X-ray topograph.

Figure 12:
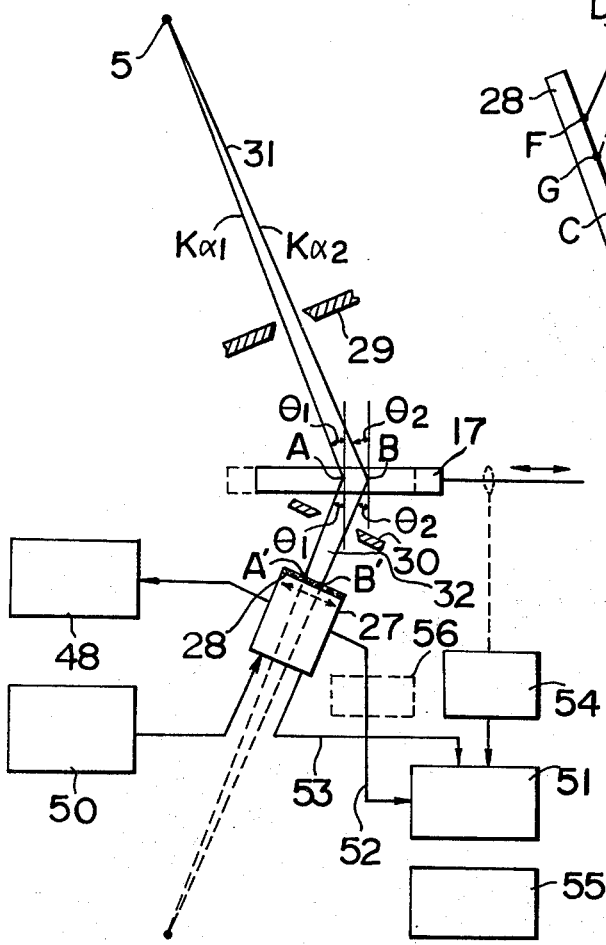
FIGS. 12 and 13 show diagrammatically still other embodiments of the X-ray topograph reproducing apparatus according to the invention wherein use is made of a television camera for the purpose of preventing a deterioration of the resolving power caused by the aberration produced by the difference in diffraction directions of two spectral lines $K\alpha_1$ and $K\alpha_2$ of the characteristic X-ray.

In FIG. 12 there is shown another embodiment of the apparatus according to the invention. In the present embodiment, the television camera 27 is made stationary, whereas the crystal 17 is made reciprocated in a direction shown by arrows and in parallel with the surface thereof in a manner such that the Bragg's diffraction condition is satisfied. As described above with reference to the embodiment shown in FIG. 6, the lattice defect point A on the crystal 17 where the $K\alpha_1$ and $K\alpha_2$ spectral lines satisfy the Bragg's diffraction condition is reproduced at two points A' and B' on the record surface 28 separated one from the other thus deteriorating the resolving power of the record thus obtained.

In the present embodiment, the record surface 28 of the television camera such as a Vidicon tube is scanned in a vertical direction (that is, in a direction perpendicular to the sheet of FIG. 12 which is the lengthwise direction of the slits 29 and 30) and furthermore the total surface of the record surface 28 inclusive of the points A' and B', that is, the region for reproducing the diffracted image is horizontally scanned in a direction shown by dotted lines arrows in FIG. 12.

For this purpose, to the camera 27 is connected an adjustable circuit 50 for adjusting the positions, amplitude and inclination of the vertical and horizontal scannings and the monitor 48 for directly viewing the condition of the record surface 28. The adjustable circuit 50 serves to properly move the position on the record surface 28 at which the vertical scanning is effected in directions shown by dotted line arrows in FIG. 12 such that said position includes the diffracted image of the X-ray having a desired wave length range, for example, the diffracted image A' of the $K\alpha_1$ line while directly viewing the monitor 48. The adjustable circuit 50 and the monitor 48 further adjust the desired wave length width, that is, the scanning amplitude in the horizontal direction (direction shown by dotted line arrows in FIG. (2) in a manner such that the scanning width is made reduced so as to scan, for example, the diffracted image A' only.

Thus, the camera 27, the adjustable circuit 50 and the monitor 48 can select the wave length and its width of the X-ray 31 at will thereby scanning the desired record surface 28 only. This is equivalent to the presence of a mechanical slit arranged in front of the record surface 28. Such mechanical slit may also be incorporated into the present embodiment.

51 designates a charge storage tube to which are delivered through condensor 52 and 53 the image reproducing output signal and the vertically scanning signal in synchronism with the vertical deflecting output from the camera tube of the camera 27, respectively. Further, provision is made of a detector circuit 54 for detecting the amount of movement of the crystal 17 which moves in a direction shown by arrows in FIG. 12. As the detector circuit 54 use may be made of a circuit comprising a potentiometer whose variable brush is connected to a standard voltage source. The variable brush is adjustably moved in response to the movement of the crystal 17 to detect the amount of movement thereof in the form of sawtooth wave signal. The detector circuit 54 is connected to the charge storage tube 51 so as to horizontally scan the vertically diffracted image of the crystal 7 in association with the amount of movement thereof. Thus, if the crystal 17 moves the diffracted image obtained by the X-ray having a given range of wave lengths can be stored in the charge storage tube 51 in two dimensional manner one by one. If the crystal 17 is reciprocated several times or the horizontal scanning of the charge storage tube 51 is effected at a low speed, the strength of the diffracted image can be increased.

To the charge storage tube 51 is coupled to direct viewing means 55. The output of the charge storage tube 51 is delivered to the direct viewing device 55 so as to directly view the diffracted image stored in the charge storage tube 51.

In place of limiting the scanning zone, use may be made of a gate circuit 56 shown by dotted lines so as to extract the image reproducing output corresponding to the X-ray topograph having a given range of wave lengths only. That is, the adjustable circuit 50 is adjusted such that the record surface 28 is vertically scanned in correspondence with the lengthwise direction of the slits and that the total surface of the record surface 28 across the points A' to B' at which is reproduced the diffracted image is horizontally scanned in directions shown by dotted line arrows to derive the image reproducing output signal. This output signal is delivered to the gate circuit 56 and by viewing the monitor 48 in comparison with the direct viewing means 55 it is possible to extract the image reproducing output signal at the desired horizontal position only. The output signal thus extracted is delivered through the conductor 52 to the charge storage tube 51.

Figure 13:
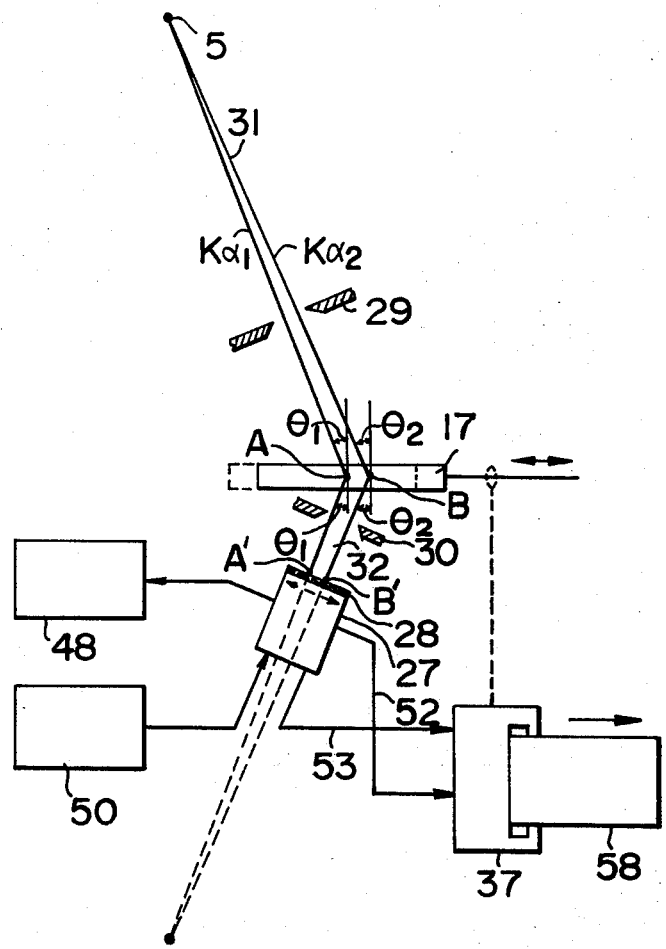

Referring to FIG. 13 there is shown a variant of the embodiment shown in FIG. 12. In the present embodiment use is made of a recording means 57 including a pin tube or a fibre tube. To the recording means 57 are supplied through the conductors 52 and 53 the image reproducing output signal and the vertical scanning signal to record the selected diffracted image on a record sheet 58 which is fed in a direction shown by an arrow response to the movement of the crystal 17. The recording means 57 may be connected in parallel with the charge storage tube 51 shown in FIG. 12. This permits of directly view and record the diffracted image.

The above mentioned embodiments shown in FIGS. 12 and 13 are applied to the Laue case is which diffracted images are obtained by X-ray transmission. These embodiments may also be applied to the Bragg case wherein diffracted images are obtained by X-ray reflection. In this case, the operation of the adjustable circuit 50 or the gate circuit 56 while directly viewing the monitor 48 is capable of obtaining the diffracted images of the X-ray having any desired range of wave lengths only.

The charge storage tube 51 may be replaced by a memory tube.

As stated hereinbefore, the invention makes it possible to electrically extract the wave length and its width of X-ray with the aid of the scanning signal of the camera or of the gate circuit; with the result that the adjustment becomes extremely simple contrary to the mechanical slit which has heretofore been used and that the lattice defect of the crystal can be detected on line in a rapid and easy manner in case of manufacturing the semiconductor wafers.

Moreover, the X-ray topograph reproducing apparatus according to the invention which is adapted to be electrically operated can remotely be controlled and hence can prevent an operator from being exposed to X-rays thus protecting him in an extremely safety manner.

It will be understood that changes may be made in the details of contruction, arrangement and operation without departing from the spirit of the invention, especially as defined in the following claims.

What is claimed is:

1. An X-ray topograph reproducing apparatus comprising
    an X-ray source which emits two characteristic X-rays $K\alpha_1$ and $K\alpha_2$ whose wave lengths are different from each other,
    means for supporting a specimen to be observed and for moving said specimen in a direction such that the distance between the X-ray source and the surface of the specimen is kept nearly constant,
    a first slit fixedly arranged between said X-ray source and said specimen supporting means, said slit for allowing passage of an incident beam to the specimen which beam is divergent enough for satisfying the Bragg reflection condition for both the $K\alpha_1$ and $K\alpha_2$ radiations,
    means for supporting a record medium substantially perpendicular to the characteristic radiations $K\alpha_1$ and $K\alpha_2$ diffracted from the specimen and for moving said record medium in synchronization with said specimen,
    a second slit fixedly arranged between said specimen supporting means and said record medium supporting means so that both of the characteristic X-rays $K\alpha_1$ and $K\alpha_2$ diffracted from said specimen can pass through said second slit, and
    means for mechanically interlocking said specimen and record medium supporting means and for moving them in proportion with respect to each other such that the characteristic radiations $K\alpha_1$ and $K\alpha_2$ diffracted by a point in the specimen are superimposed on the surface of the record medium.

2. An X-ray topograph reproducing apparatus as claimed in claim 1 and further comprising an X-ray sensitive television camera fixedly disposed to receive diffracted $K\alpha_1$ and $K\alpha_2$ radiations, a monitor connected to said television camera and for reproducing diffracted X-ray images of said specimen, and recording means with a record medium for recording said X-ray images of said specimen and for moving said record medium in synchronization with the motion of said specimen supporting means.

3. An X-ray topograph reproducing apparatus as claimed in claim 1 wherein said X-ray source includes an X-ray tube.

4. An X-ray topograph reproducing apparatus comprising
    an X-ray supply source which emits two characteristic X-rays $K\alpha_1$ and $K\alpha_2$ whose wave lengths are different from each other,
    means for supporting a specimen to be observed and for moving said specimen in such a direction that the distance between the X-ray source and the specimen is kept nearly constant,
    a first slit fixedly arranged between said X-ray supply source and said specimen supporting means, said slit for allowing passage of an incident beam to the specimen which beam is divergent enough for satisfying the Bragg reflection condition for both the $K\alpha_1$ and $K\alpha_2$ radiations,
    a second slit fixedly arranged so that both of the characteristic X-rays $K\alpha_1$ and $K\alpha_2$ diffracted from said specimen can pass through said second slit,
    an X-ray sensing television camera for receiving said two diffracted characteristic radiations $K\alpha_1$ and $K\alpha_2$,
    a detector means mechanically connected to said specimen supporting means and for producing an electric signal indicating the position on the specimen where one of the two characteristic radiations $K\alpha_1$ and $K\alpha_2$ satisfies the Bragg condition during the motion of the specimen,
    a gate circuit connected to said X-ray sensing television camera and said detector means, for extracting an image reproducing output signal due to one of the two diffracted radiations $K\alpha_1$ and $K\alpha_2$ during the motion of the specimen,
    a charge storage tube connected to both said gate circuit and detector means, for successively storing the image due to said output signal from said gate circuit at positions on the image storage surface in the storage tube corresponding to the detected positions on the specimen, and
    a direct viewing means connected to said charge storage tube, for directly viewing the image stored in said charge storage tube.

5. An X-ray topograph reproducing apparatus as claimed in claim 4 and further comprising a recording means connected to said X-ray sensing television camera, for receiving both an image reproducing output signal from said gate circuit and a vertical scanning signal from said X-ray sensing television camera, and said recording means including a record sheet moved in synchronization with the motion of the specimen, for recording a diffracted image thereon.

* * * * *